US00PP08021P

United States Patent [19]

Taylor

[11] Patent Number: Plant 8,021

[45] Date of Patent: Nov. 3, 1992

[54] NECTARINE TREE NAMED BIG JIM

[75] Inventor: James W. Taylor, Dinuba, Calif.

[73] Assignee: Ito Packing Company, Reedley, Calif.

[21] Appl. No.: 587,854

[22] Filed: Sep. 25, 1990

[51] Int. Cl.[5] ..... A01H 5/00
[52] U.S. Cl. ..... Plt./41.1
[58] Field of Search ..... Plt./41

*Primary Examiner*—James R. Feyrer
*Attorney, Agent, or Firm*—Dennis B. Haase

[57] ABSTRACT

A new and novel F2 hybrid, large size nectarine tree from "Red Jim"×"Summer Grand", bearing large fruit having yellow flesh which is red flecked to streaked most prevalently at the suture line; having very firm meaty flesh which clings to comparatively large stones at ripening which occurs at abut the June 9 to about June 22; and, with a bright, nearly total red skin color. Fruit is of excellent storing, shipping and even ripening quality and can be stored on the tree until completion of final swell.

1 Drawing Sheet

BACKGROUND OF THE VARIETY

The present invention relates to a new and distinct variety of nectarine tree, which I refer to as Big Jim, of a yellow fleshed, cling stone fruit, attractive in appearance, maturing in the early season period, which was developed from a continued fruit breeding program.

ORIGIN AND ASEXUAL REPRODUCTION OF THE NEW VARIETY

This novel nectarine was derived from an ongoing fruit breeding program for the improvement of peaches and nectarines to enhance quality and market acceptability. The flowers of the Red Jim variety (U.S. Plant Pat. No. 4,518) were emasculated and pollenated with pollen from the Summer Grand (U.S. Plant Pat. No. 2,879). Seeds produced from this method were stratified and grown to a height of about 18 inches. These seedlings were bud grafted into dehorned orchard trees in the experimental orchard of Ito Packing Co., Inc., Reedley, Calif. An F2 generation was then grown from which this selection was made and propagated into a mature dehorned tree.

As the hybrid clones matured, selections were made and retained. Flowers of such clones were open pollinated and allowed to bear fruit. Stones selected from certain of the selected clones were then planted and seedlings attained were then grafted onto dehorned trees, allowed to produce fruit, and served as an F2 generation for further selection. The tree of this application was selected from the F2 generation as an outstanding variety, and was further grafted on to several dehorned trees. Such testing has shown the clones to be identical to the outstanding selection in every distinguishing respect.

SUMMARY OF THE VARIETY

The instant variety developed through the above method was selected because of its excellent eating quality, its red basic color and late spring of maturity.

BRIEF DESCRIPTION OF THE DRAWINGS

The accompanying drawing illustrates typical specimens of the fruit and foliage of my new variety as grown in the San Joaquin Valley of California. Three specimens are shown, one of which is in the side elevation and the other from the apex view; yet another specimen is a section side elevation illustrating the internal texture and color of the flesh and pit.

DETAILED DESCRIPTION

The following is a detailed description of my new variety with color reference being to the Maerz and Paul Dictionary of Colors, except in instances where terminology having generally accepted meaning is employed.

Parentage: Red Jim×Summer Grand F2.
Propagation: Maintains its distinguishing characteristics through several bud grafts.
Locality where grown and observed: Near Reedley, County of Fresno, Calif.

TREE

Size: Large; vigorous; spreading; open; vase form; new growths tend to grow a short distance then branch; productive; percent of flowers setting to develop into fruit is less than in many varieties leading to more leaves per fruit with larger fruit with less thinning costs.
Vigor: Vigorous; productive.
Regularity of bearing: Regular bearer.
Trunk: Medium size; medium texture.
Branches: Spreading.
Leaves:
- *Color.*—Top side — 32B10; underside 31I8.
- *Size.*—Average length — 158 mm; average width 48 mm; medium thickness.
- *Margin.*—Glandular; crenate.
- *Petiole.*—Medium length; medium thickness.
- *Glands.*—Average number — two; small in size; globose; position — usually two at the base of the leaf blade near the attachment of the petiole and occasionally one at the base of the leaf blade or may be wanting; very occasionally one may be found on the stem near the base of the leaf blade.
- *Stipules.*—Small; dehisce when leaves are very young.

Flower bud: Large.
Flowers: Large; showy; average width 49 mm.
Petals: Average width 15 mm; average length 21 mm.

Color: Light pink, turning to a deep rose pink as the flower ages.

Date of bloom: About 5 days later than Red Jim (U.S. Plant Pat. No. 4,581). Bloom date is approximately March 1, however, exact dates of bloom have not been recorded.

Anthers: Light red.

FRUIT

Maturity:

*When described.*—Firm ripe — Jun. 9, 1988.

Date of first picking: Jun. 9, 1989.

Date of last picking: Jun. 22, 1989.

Size:

*Average axial length.*—77 mm; average transverse width in suture plane — 73 mm.

*Axial diameter.*—74 mm.

Form: Essentially round, but compressed at the base. Often slightly larger on right half, but may be larger on half of the fruit to left of the ventral suture.

Suture: In general, the ventral suture is shallow from the base to the apex, but may be deeper in occasional fruits. The dorsal suture extends to slightly beyond the apex with the apex sunken below the contour of the fruit.

Ventral surface:

*Cavity.*—Round, shallow.

*Base.*—Flattened slightly.

*Apex.*—Smooth with slight point; recessed in the suture.

Skin:

*Thickness.*—Medium thick; medium texture.

*Tendency to crack.*—None observed.

*Bloom.*—Wanting.

*Color.*—Base color yellow (10L6), but only around the base of the fruit where it is pressed against the limb. As the fruit matures from a basic green yellow color, it becomes very closely speckled with red dots (5J10) which coalesce to solid light red (5K6) as it matures, it then becomes a very dark shiney red (6L6) when fully mature.

Flesh:

*Texture.*—Very firm, meaty.

*Color.*—Yellow with reddish tinge (9J2). The red (5E6) color is more obvious along the suture line and around pit.

*Juice.*—Abundant.

*Flavor.*—Good balance of acid and sugar. Sweeter than many nectarines at this season with soluble solids of 16% (refractometer).

*Aroma.*—Not very pronounced.

*Fibres.*—Considerable around pit with many running out into the flesh.

*Ripening.*—Even, remains firm on the tree for a long period so that it can be harvested and packed after making its final swell.

*Eating quality.*—Excellent.

Stone:

*Adherence to the flesh.*—Cling stone.

*Size.*—Average thickness 19 mm; average width 31 mm; average length 42 mm. Pit is considerably larger than that of most early maturing varieties.

*Form.*—Oval.

*Hilum.*—Small, oblong.

*Dorsal edge.*—Shallow grooves.

*Ventral edge.*—Narrow, almost continuous groove from the base to hear the apex; pronounced wing in the upper one third.

*Surface.*—Irregular deep in the upper one-third of the pit.

*Color.*—Brown (7L12) shade to reddish brown throughout (47L1).

Use: Fresh market.

Keeping quality: Excellent.

Shipping quality: Excellent.

Resistance of disease: Similar to other glanded varieties of nectarines.

Although this novel nectarine possesses the described characteristics as a result of the growing conditions in the Reedley area of Fresno County, Calif., in the central portion of the San Joaquin Valley, it is to be understood that variations of the usual magnitude in characteristics incident to growing conditions, fertilization, pruning and pest control are to be expected.

Having thus described and illustrated my new nectarine tree, what is new and desired to be secured by Letters Patent is:

1. A new and distinct variety of nectarine tree with fruit of yellow fleshed cling stone type, substantially as herein shown and described, having a maturity period in the early spring season, having fruit of good sugar content, the fruit being large, essentially round, with deep red color over much of the exterior, particularly when fully mature, with flesh of yellow with reddish tinge, the red being more obvious around the pit and suture line.

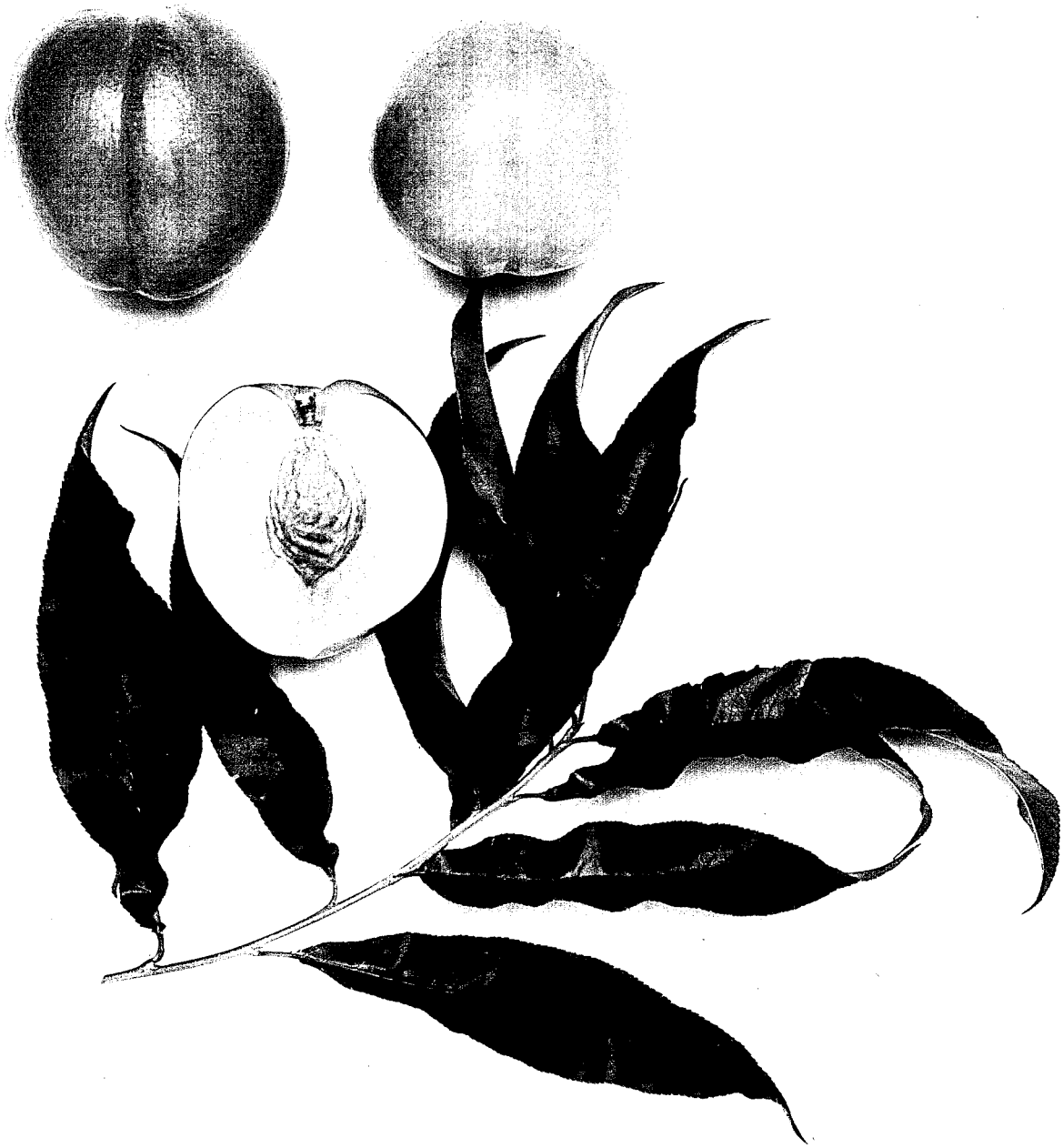

* * * * *